(12) United States Patent
Choi et al.

(10) Patent No.: US 12,569,422 B2
(45) Date of Patent: *Mar. 10, 2026

(54) COMPOSITION AND METHOD OF INHIBITING CORTISONE REDUCTASE BY APPLYING IT TO THE SKIN

(71) Applicant: AMOREPACIFIC CORPORATION, Seoul (KR)

(72) Inventors: Eun Jeong Choi, Yongin-si (KR); Young Gyu Kang, Yongin-si (KR); Jihyun Kim, Yongin-si (KR); Euidong Son, Yongin-si (KR); Gayoung Cho, Yongin-si (KR); Sowoong Choi, Yongin-si (KR); Hyoung June Kim, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 787 days.

This patent is subject to a terminal disclaimer.

(21) Appl. No.: 17/284,643

(22) PCT Filed: Oct. 10, 2019

(86) PCT No.: PCT/KR2019/013309
§ 371 (c)(1),
(2) Date: Apr. 12, 2021

(87) PCT Pub. No.: WO2020/076104
PCT Pub. Date: Apr. 16, 2020

(65) Prior Publication Data
US 2021/0393496 A1 Dec. 23, 2021

(30) Foreign Application Priority Data

Oct. 10, 2018 (KR) ........................ 10-2018-0120692

(51) Int. Cl.
*A61K 8/49* (2006.01)
*A23L 33/10* (2016.01)
*A61Q 19/00* (2006.01)

(52) U.S. Cl.
CPC .............. *A61K 8/498* (2013.01); *A61Q 19/00* (2013.01); *A23L 33/10* (2016.08); *A23V 2200/318* (2013.01); *A23V 2250/30* (2013.01); *A61K 2800/782* (2013.01)

(58) Field of Classification Search
CPC ... A61K 8/498; A61K 2800/782; A61Q 19/00
See application file for complete search history.

(56) References Cited

U.S. PATENT DOCUMENTS

| | | | |
|---|---|---|---|
| 6,334,998 B1 | 1/2002 | Uckun et al. | |
| 9,265,707 B2 * | 2/2016 | Jeon ........................ | A61P 31/04 |
| 9,655,878 B2 * | 5/2017 | Jeon ........................ | A61P 3/04 |
| 10,111,856 B2 * | 10/2018 | Shin ........................ | A61K 36/48 |
| 10,959,981 B2 * | 3/2021 | Shin ........................ | A61K 31/37 |
| 2005/0137176 A1 | 6/2005 | Ferraris et al. | |
| 2013/0028921 A1 | 1/2013 | Jeon et al. | |
| 2013/0071342 A1 | 3/2013 | Jeon et al. | |
| 2013/0090377 A1 | 4/2013 | Jeon et al. | |

FOREIGN PATENT DOCUMENTS

| | | |
|---|---|---|
| CN | 102905685 A | 1/2013 |
| CN | 102905714 A | 1/2013 |
| EP | 1547578 A2 | 6/2005 |
| JP | 6-321763 A | 11/1994 |
| JP | 2008-120729 A | 5/2008 |
| JP | 2012-219014 A | 11/2012 |
| JP | 2016-526019 A | 9/2016 |
| KR | 2002-0000980 A | 1/2002 |
| KR | 10-0706279 B1 | 4/2007 |
| KR | 10-2011-0110052 A | 10/2011 |
| KR | 10-2012-0061771 A | 6/2012 |
| KR | 10-2013-0079220 A | 7/2013 |
| KR | 10-1384497 B1 | 4/2014 |
| KR | 10-1433539 B1 | 8/2014 |
| KR | 10-2014-0131881 A | 11/2014 |
| KR | 10-2018-0071591 A | 6/2018 |
| KR | 10-2018-0090604 A | 8/2018 |
| WO | 2014/106848 A1 | 7/2014 |

OTHER PUBLICATIONS

Bianchi et. al. ((2018), Coumestrol/hydroxypropyl-ß-cyclodextrin association incorporated in hydroxypropyl methylcellulose hydrogel exhibits wound healing effect: in vitro and in vivo study, European Journal of Pharmaceutical Sciences, 119, 179-188) (Year: 2018).*
Choe et. al. ((2018), Psychological Stress Deteriorates Skin Barrier Function by Activating 11ß-Hydroxysteroid Dehydrogenase 1 and the HPA Axis, Scientific Reports, 8, 1-11). (Year: 2018).*
McDermott ((2017), How Can I Get Ride of Forehead Wrinkles, Health Line, (https://www.healthline.com/health/beauty-skin-care/forehead-wrinkles#takeaway) accessed: Nov. 15, 2024 (Year: 2017).*
Orion et. al. ((2012), Psychological stress and epidermal barrier function, Clinics in Dermatology, 30, 280-285) (Year: 2012).*
Elissa S Epel, "Psychological and metabolic stress: A recipe for accelerated cellular aging?", Hormones, 2009, vol. 8, No. 1, pp. 7-22 (16 pages total).
Ari Levine et al., "Measuring cortisol in human psychobiological studies", Physiology & Behavior, 2007, vol. 90, pp. 43-53 (11 pages total).
Ying Chen et al., "Brain-Skin Connection: Stress, Inflammation and Skin Aging", Inflammation & Allergy—Drug Targets, 2014, vol. 13, No. 3, pp. 177-190 (14 pages total).

(Continued)

*Primary Examiner* — Juliet C Switzer
*Assistant Examiner* — Dawanna Shar-Day White
(74) *Attorney, Agent, or Firm* — Sughrue Mion, PLLC

(57) ABSTRACT

Provided are a composition including coumestrol extracted from soybeans as an active ingredient, and a method of inhibiting cortisone reductase by applying it to skin of a subject.

2 Claims, 3 Drawing Sheets

(56) References Cited

OTHER PUBLICATIONS

Claudia A. Staab et al., "11ß-Hydroxysteroid dehydrogenase type 1 is an important regulator at the interface of obesity and inflammation", Journal of Steroid Biochemistry and Molecular Biology, 2010, vol. 119, pp. 56-72 (17 pages total).

John W. Newcomer et al., "Decreased Memory Performance in Healthy Humans Induced by Stress—Level Cortisol Treatment", Arch Gen Psychiatry, Jun. 1999, vol. 56, pp. 527-533 (7 pages total).

Extended European Search Report issued Jun. 21, 2022 in European Application No. 19871298.6.

Gaeun Park et al., "Flt3 is a target of coumestrol in protecting against UVB-induced skin photoaging", Biochemical Pharmacology, 2015, pp. 473-483, vol. 98.

Sung Jay Choe et al., "Psychological Stress Deteriorates Skin Barrier Function by Activating 11ß-Hydroxysteroid Dehydrogenase 1 and the HPA Axis", Scientific Reports, Apr. 20, 2018, pp. 1-11, vol. 8, 6334.

Charles H. Blomquist et al., "Inhibition of 3α-hydroxysteroid dehydrogenase (3α-HSD) activity of human lung microsomes by genistein, daidzein, coumestrol and C18-, C19- and C21-hydroxysteroids and ketosteroids", Steroids, 2005, pp. 507-514, vol. 70.

International Searching Authority, International Search Report for PCT/KR2019/013309, dated Jan. 29, 2020.

* cited by examiner

FIG. 1

COMPOSITION AND METHOD OF INHIBITING CORTISONE REDUCTASE BY APPLYING IT TO THE SKIN

CROSS REFERENCE TO RELATED APPLICATION

This application is a National Phase Patent Application and claims priority of International Application Number PCT/KR2019/013309, filed Oct. 10, 2019 which claims priority to and the benefit of Korean Patent Application No. 10-2018-0120692 filed in the Korean Intellectual Property Office on Oct. 10, 2018, the entire contents of each is incorporated herein by reference.

TECHNICAL FIELD

This disclosure relates to a composition and a method of inhibiting cortisone reductase by applying it to the skin.

BACKGROUND ART

Stress has been called a root of all illnesses since ancient times, and particularly in modern society, stress has excessively occurred because of various reasons such as social factors of study, work, marriage, parenting, and the like, and environmental factors such as weather, traffic, and the like for anyone regardless of sex or age, so it is recognized as a very serious social problem.

As our society has rapidly developed and diversified, roles required of modern people are increased, so that people suffering generalized anxiety disorders and mental disorders caused by many types of stress have increased. According to "A Study on Epidemiology of Mental Illness in 2006" published by the Ministry of Health and Welfare, "a one-year prevalence of metal illness" which refers to a percentage of people that experienced at least one type of mental illness for the year of 2006 was found to be 17.1%. This is around one person per 6 adults from greater than or equal to 18 years old to less than or equal to 64 years old, and 'a lifetime prevalence of metal illness' which is a percentage of people who experienced at least one type of mental illness for a whole life at the moment in 2006 was found to be 30%, which is one person per 3 adults. Considering the tendency toward increasing mental illness of adolescents caused by excessive academic enthusiasm or many types of stress, the prevalence for the entire population may be considered higher than the above.

Nowadays, anxiety disorder is treated by drug treatment along with a long-term psychotherapy in a clinic, and in the case of drug treatment, benzodiazepine-based anti-anxiety drugs such as diazepam, lorazepam, clonazepam, and alprazolam are mainly used, and azapirone-based buspirone is used as a drug for selectively acting on a serotonin receptor to selectively mitigate anxiety symptoms. In addition, recently, researches on stress controlling materials derived from natural materials capable of compensating side effects of these drugs have been actively performed.

The present inventors continuously researched substances derived from natural products capable of preventing or treating mental stress-related diseases and have confirmed that in a mental stress situation, 11β-hydroxysteroid dehydrogenase type 1, cortisone reductase of keratinocytes present in the epidermis, is activated, increasing a concentration of cortisol in the epidermis (increasing a reduction degree from cortisone to cortisol), and in addition, skin barrier function deterioration phenomenon due to the activation of the 11β-hydroxysteroid dehydrogenase type 1 shows a completely different mechanism from that caused by other causes (e.g. physical injury or aging, etc.) not by the mental stress. Furthermore, it has been confirmed that coumestrol extracted from soybean specifically inhibits the activity of the 11β-hydroxysteroid dehydrogenase type 1 , thereby completing one aspect of the present disclosure.

On the other hand, the coumestrol is a substance mainly found in seeds, roots, and leaves of leguminosae and compositae plants and generally is classified into a coumestan-based compound as a type of isoflavonoid. The coumestrol is an ingredient that is little or no in general soybeans and is produced only when soybeans are germinated (Food Sci. Biotechnol., 12(3), 278-284, 2003), and in addition, as the initial germination date increases, a content of the coumestrol is known to increase (J Agric Food Chem., 48(6), 2167-2172, 2000). In addition, the coumestrol is known to promote the production of connective tissues such as collagen and the like in skin and organs, even though the exact mechanism is not known, and thus is estimated to have an effect of inhibiting aging or wrinkles in terms of histology (Bickoff, E. M., et al., J. Anim. Sic., 19, 4 (1960)).

Furthermore, Japanese Patent Pyeung No. 5-286865 discloses a formulation composition reducing a blood fat concentration of cholesterol and triglycerides, which are the most important risk factors for cardiovascular diseases and myocardial infraction, by using an Alfalfa forsythia extract containing coumestrol, and Korean Patent No. 10-2002-0000980 discloses skin cosmetics containing 3,9-diferulyl coumestrol having strong antioxidant activity and also promoting revitalization of skin connective tissues and thus exhibiting anti-aging and skin whitening effects by synthesizing coumestrol and then, ester-linking the synthesized coumestrol with ferulic acid to synthesize the 3,9-diferulyl coumestrol.

However, in the aforementioned conventional inventions, the coumestrol is not completely known to prevent or treat the deterioration of the skin barrier function by inhibiting the activity of the cortisone reductase (11β-hydroxysteroid dehydrogenase 1) caused by the mental stress.

DISCLOSURE

Technical Problem

In an embodiment, a (cosmetic) composition capable of shortening the time of recovering a barrier function of the stratum corneum is provided by inhibiting the activity of 11β-hydroxysteroid dehydrogenase type 1, which is a factor in reducing skin barrier function due to mental stress and thus, by reducing the concentration of cortisol caused by mental stress.

Technical Solution

According to an embodiment, a composition for inhibiting cortisone reductase includes coumestrol extracted from soybeans as an active ingredient.

The cortisone reductase may be 11β-hydroxysteroid dehydrogenase type 1.

The coumestrol may be included in a concentration range of 0.001 μM to 1,000 μM.

The soybeans may include beans selected from soybean peas and mung beans, germinated beans germinated from the beans, or a combination thereof.

The composition may be a cosmetic composition.

According to another embodiment, provided is a method of inhibiting cortisone reductase by applying a composition including an effective amount of cumestrol extracted from soybeans as an active ingredient, to the skin.

Advantageous Effects

According to an embodiment, the time of recovering a barrier function of the stratum corneum may be shortened by inhibiting the activity of 11β-hydroxysteroid dehydrogenase type 1, which is a factor in decreasing skin barrier function due to mental stress, and thus by reducing the concentration of cortisol caused by mental stress. That is, it is possible to specifically prevent and treat the phenomenon of decreasing skin barrier function caused by mental stress among various causes of decreasing skin barrier function.

DESCRIPTION OF THE DRAWINGS

FIG. 1 is a result of measuring the concentration of cortisol in a cell culture solution using an ELISA method.

BEST MODE

Figure 2:
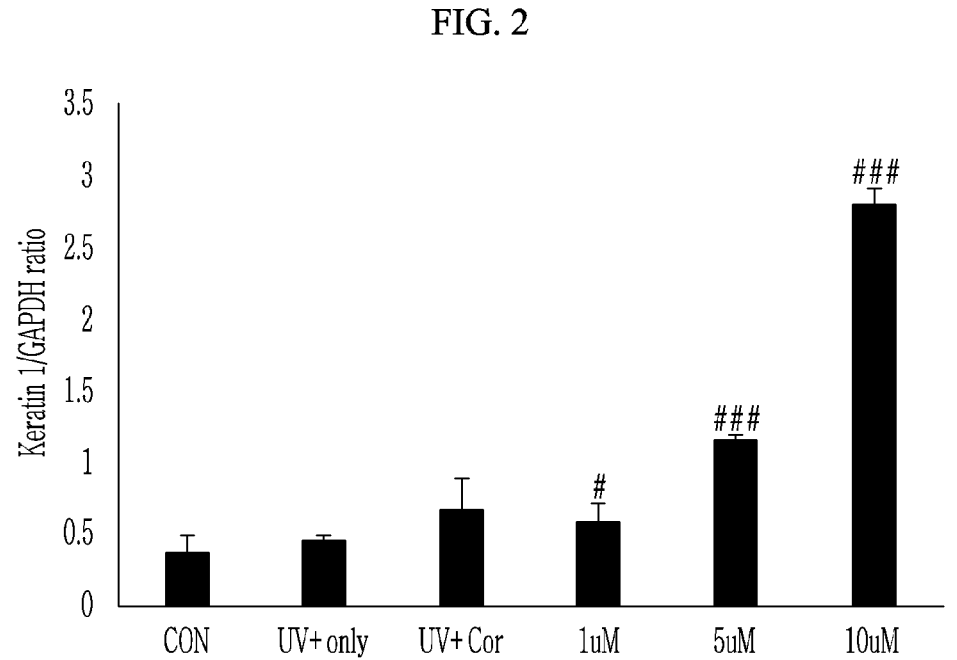
FIG. 2 is a western blotting photograph to confirm the protein expression of keratin 1, which is a keratinocyte differentiation marker.

Hereinafter, embodiments of one aspect of the present disclosure are described in detail so that those of ordinary skill in the art can easily implement one aspect of the present disclosure. However, this disclosure may be embodied in many different forms and is not construed as limited to the example embodiments set forth herein.

In the present specification, the improvement of skin barrier function means reducing a concentration of cortisol by inhibiting the activity of 11β-hydroxysteroid dehydroge- nase type 1 present in the damaged skin area due to mental stress, which is irrelevant in suppressing an oxidation stress or maintaining skin homeostasis and the like caused by physical damage or aging or the like. This is because the suppressing oxidation stress or the maintaining skin homeo- stasis, and the like are not caused by mental stress, so the mechanism is totally different.

In addition, in the present specification, the mental stress does not mean a neurosis as referred to in a medical field, which means a maladapted status since a patient cannot adaptively adjust to psychological stress, but means a status of well adjusting to psychological stress but activating cortisone reductase (11β-hydroxysteroid dehydrogenase type 1) of keratinocytes in the epidermis regardless of the will of the parts concerned.

In the present specification, it will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise pro- vided, the term "combination" refers to mixing or copoly- merization. In addition, "copolymerization" means block copolymerization or random copolymerization, and "copo- lymer" means block copolymer or random copolymer.

Hereinafter, a composition for inhibiting cortisone reductase according to an embodiment is described.

A composition for inhibiting cortisone reductase accord- ing to an embodiment includes coumestrol extracted from soybeans as an active ingredient.

Since the coumestrol extracted from soybeans specifically inhibits the activity of cortisone reductase present in kera- tinocytes in the epidermis under a mental stress situation, the composition according to an embodiment may prevent dete- rioration of a skin barrier function even under the mental stress situation or rapidly improve the skin barrier function that is weakened by mental stress.

Specifically, under mental stress, since wound healing is delayed, and the skin barrier function is deteriorated, the firmness of the stratum corneum is also deteriorated, or recovery of the skin barrier function after the damage is delayed, which may be explained by two mechanisms. One mechanism is as follows; the metal stress activates an HPA (hypothalamus pituitary adrenal) axis to increase secretion of glucocorticoids (GC) in the blood through, and the glucocorticoids (GC) binds to GC receptors (GR) present in the epidermis and dermis, which are peripheral tissues, resulting in deteriorating the skin barrier function. The other mechanism is as follows; the mental stress activates corti- sone reductase (11β-hydroxysteroid dehydrogenase 1) of keratinocytes in the epidermis, thereby increasing a concen- tration of cortisol (an activated GC form) and resulting in deteriorating the skin barrier function. The composition according to an embodiment may prevent the deterioration of the skin barrier function by inhibiting the activation of the cortisone reductase (11β-hydroxysteroid dehydrogenase 1) according to the second mechanism.

The cortisone reductase may be 11β-hydroxysteroid dehydrogenase type 1. The coumestrol extracted from soy- beans and included in the composition according to an embodiment as an active ingredient may specifically act on the 11β-hydroxysteroid dehydrogenase type 1 and thus inhibit the activation of the cortisone reductase.

Accordingly, an embodiment provides a composition for inhibiting cortisone reductase including coumestrol extracted from soybeans as an active ingredient and specifi- cally, a composition for inhibiting activation of 11β-hydrox- ysteroid dehydrogenase type 1, which may include a phar- maceutically effective amount of the coumestrol alone or along with at least one pharmaceutically acceptable carrier, excipient, or diluent.

The soybeans may include beans selected from soybean peas and mung beans, germinated beans germinated from the beans, or a combination thereof. Specifically, the com- position for inhibiting cortisone reductase according to an embodiment may include coumestrol or a natural product containing the coumestrol and its extract as an active ingre- dient, and the coumestrol or the natural product containing and its extract may be obtained from beans such as soy- beans, peas, and mung beans, germinated beans germinated from the beans, or a combination thereof. In addition, the extract of the natural product containing the coumestrol may be obtained by collecting an extract through cold precipita- tion at room temperature or warm precipitation of the natural product containing the coumestrol with 70% ethanol, com- pletely concentrating it, dispersing it again in water, and fractionally collecting it again with at least one or two solvents selected from hexane, dichloromethane, chloro- form, ethylacetate, butanol, ethanol, methanol, and water in the same amount. However, the extraction method is not limited thereto but may include all extraction methods of containing the coumestrol in a final product.

In the composition, the cumestrol may be included in a concentration range of 0.001 μM to 1,000 μM, for example, 0.001 μM to 100 μM. When the cumestrol is used as a cosmetic composition for inhibiting cortisone reductase, the cumestrol may be used at a concentration of greater than or equal to 0.001 μM, greater than or equal to 0.01 μM. The cumestrol may be used at a concentration of less than or equal to 1,000 μM, less than or equal to 100 μM. When the coumestrol is used at a concentration of less than 0.001 μM, there may be insignificant effects of proliferating epidermal keratinocytes and improving the skin battier function, but when the coumestrol is used at a concentration of greater than 1,000 μM, cytotoxicity may appear and thus harm the human body, which is not desirable.

In the above, "pharmaceutically effective amount" refers to an amount sufficient to allow the physiologically active ingredient to be administered to an animal or human to exhibit desired physiological or pharmacological activity. However, the effective amount of the pharmaceutical may vary according to the degrees of symptoms, ages, weights, health status, sexes, administration routes, and duration of treatment.

In addition, "pharmaceutically acceptable" refers to physiologically acceptable when administered to humans, and usually does not cause allergic reactions or similar reactions, such as gastrointestinal disorders or dizziness. Examples of the carrier, excipient, and diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oils. In addition, it may further include fillers, anticoagulants, lubricants, wetting agents, fragrances, emulsifiers, and antiseptics.

For example, the composition may be a cosmetic composition.

In the present specification "cosmetic" may refer to any material that may have a medical function in addition to the cosmetic function.

The formulation of the cosmetic composition is not particularly limited and may be appropriately selected as desired.

For example, the cosmetic composition may be formulated into formulations such as solutions, suspension liquids, emulsions, pastes, gels, creams, lotions, powders, soaps, surfactant-containing cleansings, oils, powder foundations, emulsion foundations, wax foundations, and sprays, but is not limited thereto. More specifically, it may be formulated into cosmetic compositions such as detergents, tonics, hair dressings, nourishing lotions, essences, serums, treatments, conditioners, shampoos, lotions, wools, or hair dyes, and the like, and may be formulated into basic cosmetics such as an oil-in-water (O/W) type, a water-in-oil (W/O), and the like. In addition, in the composition, in addition to the above-mentioned essential components in each formulation, other components may be appropriately selected and formulated without difficulty by a person of ordinary skill in the art according to types or use purposes of other external preparations. For example, ultraviolet blocking agents, hair conditioning agents, fragrances, and the like may be further included.

The cosmetic composition may include a cosmetically acceptable medium or base. These are all formulations suitable for topical applications. The cosmetic composition may be provided in the form of emulsions obtained by dispersing an oil phase in an aqueous phase, suspensions, microemulsions, microcapsules, microgranules, or ion-type (liposome) and/or non-ionized vesicle dispersing agents, or in the form of creams, skins, lotions, powders, ointments, sprays, or conceal sticks. These compositions may be prepared according to conventional methods in the art.

When the formulation of one aspect of the present disclosure is a solution or emulsion, a solvent, a solubilizer, or an emulsifier may be used as carrier components. For example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan may be used.

If the formulation of one aspect of the present disclosure is a suspension, the carrier component may be a diluent of a liquid such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, and the like.

If the formulation of one aspect of the present disclosure is pastes, creams, or gels, the carrier component may be animal oil, vegetable oil, wax, paraffin, starch, tragacanth, cellulose derivatives, polyethylene glycol, silicone, bentonite, silica, talc, or zinc oxide.

If the formulation of one aspect of the present disclosure is powders or sprays, the carrier component may be lactose, talc, silica, aluminum hydroxide, calcium silicate, or polyamide powders. Particularly, in the case of sprays, a propellant such as a chlorofluorohydrocarbon, propane/butane, or dimethyl ether may be additionally included.

In an embodiment of one aspect of the present disclosure, the cosmetic composition may include thickeners. The thickeners included in the cosmetic composition of one aspect of the present disclosure may be methyl cellulose, carboxyl methyl cellulose, carboxyl methyl hydroxy guanine, hydroxy methyl cellulose, hydroxyethyl cellulose, a carboxyl vinyl polymer, polyquaternium, cetearyl alcohol, stearic acid, and carrageenan, and preferably one or more of carboxyl methyl cellulose, a carboxyl vinyl polymer, and polyquaternium may be used, and more preferably a carboxyl vinyl polymer may be used.

In an embodiment of one aspect of the present disclosure, the cosmetic composition may include a variety of suitable bases and additives as needed, and the types and amounts of these components may be easily selected by the inventor. If necessary, it may include an acceptable additive, and may further include, for example, conventional ingredients such as antiseptics, pigments, additives, and the like.

The antiseptics may specifically be phenoxyethanol or 1,2-hexanediol, and the fragrances may be artificial fragrances.

In an embodiment of one aspect of the present disclosure, the cosmetic composition may include a composition selected from a water-soluble vitamin, an oil-soluble vitamin, a polymeric peptide, a polymeric polysaccharide, a sphingolipid, and a seaweed extract. Other ingredients that may be added include fats and oils, humectants, emollients, surfactants, organic and inorganic pigments, organic powders, ultraviolet absorbers, antiseptics, fungicides, antioxidants, plant extracts, pH adjusters, alcohols, pigments, fragrances, blood circulation accelerators, coolants, anhidrotics, purified water, and the like.

In addition, the compounding components which may be added other than these are not limited thereto. Moreover, any component may be blended in the range which does not damage the purpose and effect of the invention.

Furthermore, the cosmetic composition according to an embodiment may be used not only as a pharmaceutical composition as described above, but also as a dietary supplement. For example, it may be easily used as main ingredients, auxiliary ingredients, food ingredients, food additives, functional foods, or beverages.

The "food" means a natural or processed product including one or more nutrients, and preferably means that it is ready to be eaten directly after a certain amount of processing. It includes all foods, food additives, functional foods, and beverages.

The foods to which the food composition can be added may include, for example, various foods, beverages, gums, teas, vitamin composites, and functional foods. In addition, the foods may include special nutritional products (e.g., formulas, baby food, etc.), processed meat products, fish products, tofu, jellies, noodles (e.g. ramen noodles, etc.), breads, dietary supplements, seasoned foods (e.g., soy sauce, soybean paste, red pepper paste, mixed soy sauce, etc.), sauces, sweets (e.g. snacks), candy, chocolate, gum, ice cream, dairy products (e.g. fermented milk, cheese, etc.), other processed foods, kimchi, pickles (various kimchi, pickles, etc.), beverages (e.g., fruit beverages, vegetable beverages, soy milk, fermented beverages, etc.), and natural seasonings (e.g., ramen soup, etc.), but are not limited thereto. The foods, beverages, or food additives may be prepared by conventional manufacturing methods.

In addition, "functional foods" or "health functional foods" refers to a food group that has added values to foods by using physical, biochemical, or biotechnological techniques to act and express functions of foods for specific purposes, or foods that are processed and designed to fully express the body's regulatory functions, such as defense rhythm control of food compositions, disease prevention, and recovery of living bodies. It may specifically be a health functional food. The functional food may include acceptable food auxiliary additives, and may further include suitable carriers, excipients, and diluents commonly used in the manufacture of functional foods.

The types of dietary supplements are not limited thereto, but may be in a form of powders, granules, tablets, capsules, or beverages.

According to another embodiment, provided is a method of inhibiting cortisone reductase by applying a composition including an effective amount of cumestrol extracted from soybeans as an active ingredient, to the skin.

Advantages and features of one aspect of the present disclosure and methods for achieving them will be apparent with reference to the examples described in detail below. One aspect of the present disclosure will be described in detail with reference to examples. However, these examples are specifically provided for describing one aspect of the present disclosure, and the range of one aspect of the present disclosure is not limited to these examples.

Mode for Invention

EXAMPLES

Experimental Example 1

Inhibitory Effect of Cortisone Reductase Activity by Coumestrol

Human keratinocytes (normal human epidermal keratinocytes, NHEK) were cultured in a 6-well plate incubator.

Figure 1:
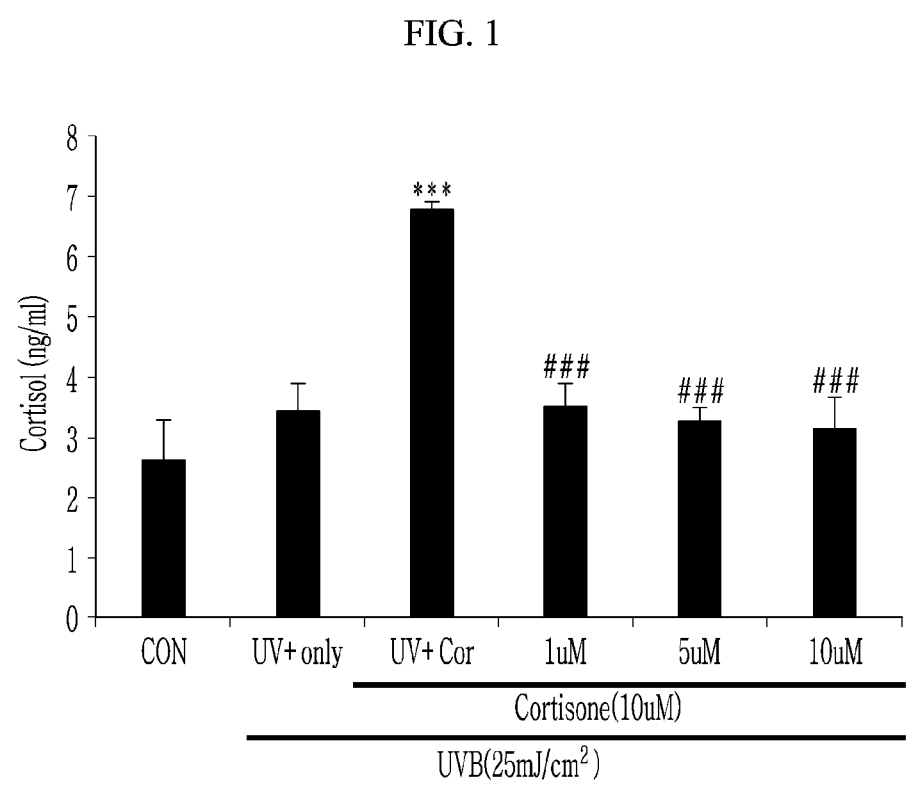

Specifically, the normal human epidermal keratinocytes were cultured by replacing it with phosphate-buffered saline (PBS) after 24 hours to irradiate UVB (25 mJ/cm$^2$) and then, adding cortisone (10 μM) to NHEK culture media having no hydrocortisone. Subsequently, the cell culture solution was collected to measure a cortisol concentration in an ELISA method, and the results are shown in FIG. 1. Referring to FIG. 1, a cortisol concentration was significantly increased in a well where cortisone was added after the ultraviolet (UV) irradiation (UVB 25 mJ/cm$^2$), compared with before the ultraviolet (UV) irradiation (CON; CONTROL), but in wells where coumestrol (1 μM, 5 μM, 10 μM) was included, the cortisol concentration was not significantly increased. Accordingly, a composition including the coumestrol as an active ingredient according to an embodiment turned out to inhibit activity of 11β-hydroxysteroid dehydrogenase type 1, a cortisone reductase

Experimental Example 2

Inhibitory Effect of Cortisone Reductase Activity by Coumestrol

Figure 3:
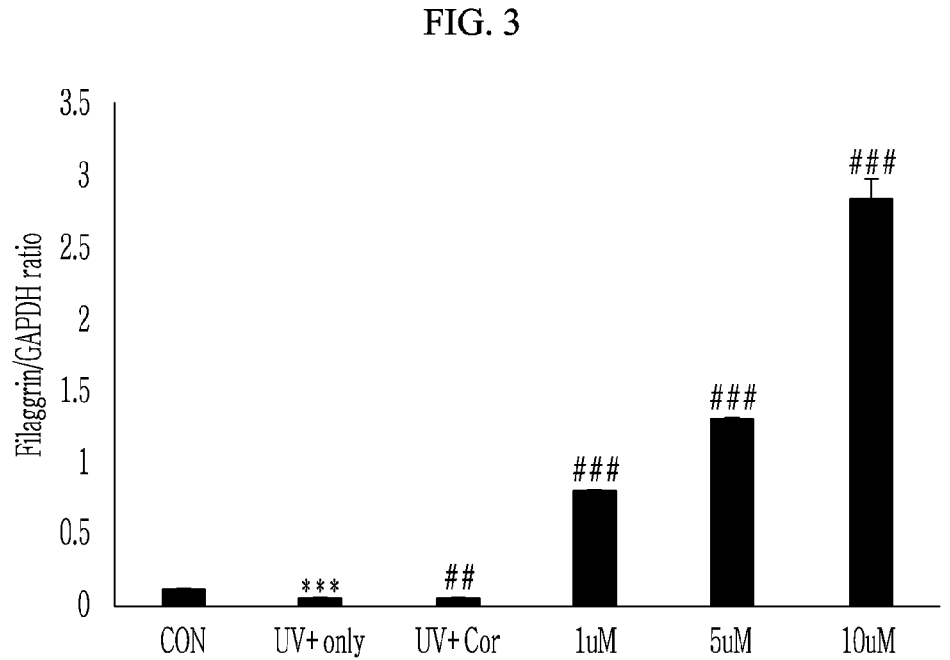
FIG. 3 is a western blotting photograph to confirm the protein expression of filaggrin, which is a marker for keratinocyte differentiation.

In addition, after separating proteins from the human keratinocytes using a RIPA lysis buffer, protein expression of keratinocyte differentiation markers (KRT1, Filaggrin) was confirmed through western blotting, and the results are shown in FIGS. 2 and 3. Referring to FIGS. 2 and 3, in the wells containing the coumestrol (1 μM, 5 μM, 10 μM), gene expression of the keratinocyte differentiation markers (KRT1, Filaggrin) inhibited by the ultraviolet (UVB) rays was increased in the keratinocytes. In other words, the gene expression of the keratinocyte differentiation markers inhibited by the ultraviolet (UVB) rays in the keratinocytes was restored by the coumestrol, and accordingly, the coumestrol inhibited activity of the cortisone reductase and reduced the cortisol concentration, eventually restoring the gene expression of the keratinocyte differentiation markers.

Although the preferred embodiments of one aspect of the present disclosure have been described in detail, the scope of one aspect of the present disclosure is not limited thereto, and various modifications and improvements by those skilled in the art using the basic concept of one aspect of the present disclosure defined in the following claims are also within the scope of the invention.

The invention claimed is:

1. A method of improving skin barrier function that has been compromised by an increase in the cortisol level within the epidermis in a subject, comprising applying an effective amount of a composition to skin of the subject, wherein the composition comprises coumestrol extracted from soybeans as an active ingredient in a concentration range of 0.001 μM to 10 μM, wherein the increase in cortisol level within the epidermis is caused by mental stress, wherein the increase in cortisol level within the epidermis caused by mental stress is simulated by UV irradiation and the addition of cortisone to human keratinocytes, and wherein the composition is a cosmetic composition.

2. The method of claim 1, wherein the soybeans comprise beans selected from soybean peas and mung beans, germinated beans germinated from the beans, or a combination thereof.

* * * * *